(12) United States Patent
Li et al.

(10) Patent No.: US 10,914,693 B2
(45) Date of Patent: Feb. 9, 2021

(54) RAY TRANSMISSION AND FLUORESCENCE CT IMAGING SYSTEM AND METHOD

(71) Applicants: Tsinghua University, Beijing (CN); NUCTECH COMPANY LIMITED, Beijing (CN)

(72) Inventors: Liang Li, Beijing (CN); Zhiqiang Chen, Beijing (CN); Li Zhang, Beijing (CN); Ziran Zhao, Beijing (CN); Yuxiang Xing, Beijing (CN); Siyuan Zhang, Beijing (CN)

(73) Assignees: Tsinghua University, Beijing (CN); NUCTECH COMPANY LIMITED, Beijing (CN)

( * ) Notice: Subject to any disclaimer, the term of this patent is extended or adjusted under 35 U.S.C. 154(b) by 218 days.

(21) Appl. No.: 16/045,243

(22) Filed: Jul. 25, 2018

(65) Prior Publication Data

US 2019/0056338 A1    Feb. 21, 2019

(30) Foreign Application Priority Data

Jul. 25, 2017  (CN) .......................... 2017 1 0616773

(51) Int. Cl.
  *G01N 23/00*  (2006.01)
  *G01N 23/2206*  (2018.01)
  (Continued)

(52) U.S. Cl.
  CPC ......... *G01N 23/2206* (2013.01); *A61B 6/035* (2013.01); *A61B 6/06* (2013.01);
  (Continued)

(58) Field of Classification Search
  CPC ......... A61B 6/035; A61B 6/107; A61B 6/485; A61B 6/5235; G01N 2223/03; G01N 2223/075; G01N 23/046; G01N 23/2206
  See application file for complete search history.

(56) References Cited

U.S. PATENT DOCUMENTS

2005/0047541 A1   3/2005  Tsuyuki
2006/0182217 A1   8/2006  Harding et al.
(Continued)

FOREIGN PATENT DOCUMENTS

CN   101862200 A   10/2010
CN   105092617 A   11/2015
(Continued)

OTHER PUBLICATIONS

Great Britain Paten Application No. 1812115.2; Examination Report; dated Oct. 15, 2019; 3 pages.
(Continued)

*Primary Examiner* — Dani Fox
(74) *Attorney, Agent, or Firm* — BakerHostetler (57) ABSTRACT

The present disclosure discloses a ray transmission and fluorescence CT imaging system and method. The system comprises: a ray source configured to emit a beam of rays; a rotational scanning device configured to perform rotational CT scanning on an object to be inspected; a transmission CT detector configured to receive the beam of rays which has passed through the object; a fluorescence CT detector configured to receive fluorescent photons excited by irradiation of the beam of rays on the object; a data acquisition unit configured to acquire a transmission data signal and a fluorescence data signal respectively; and a control and data processing unit configured to control the ray source to emit the beam of rays, control the rotational scanning device to perform the rotational CT scanning, and obtain a transmission CT image and a fluorescence CT image simultaneously based on the transmission data signal and the fluorescence data signal.

18 Claims, 3 Drawing Sheets

(51) Int. Cl.
*G01N 23/046* (2018.01)
*G01N 23/223* (2006.01)
*A61B 6/03* (2006.01)
*A61B 6/06* (2006.01)
*A61B 6/10* (2006.01)
*A61B 6/00* (2006.01)

(52) U.S. Cl.
CPC ............ *A61B 6/107* (2013.01); *A61B 6/4258* (2013.01); *A61B 6/5235* (2013.01); *G01N 23/046* (2013.01); *G01N 23/223* (2013.01); *A61B 6/4241* (2013.01); *A61B 6/485* (2013.01); *G01N 2223/03* (2013.01); *G01N 2223/076* (2013.01); *G01N 2223/1013* (2013.01); *G01N 2223/1016* (2013.01)

(56) References Cited

U.S. PATENT DOCUMENTS

| | | | |
|---|---|---|---|
| 2008/0001088 | A1 | 1/2008 | Joung |
| 2009/0159802 | A1 | 6/2009 | Beekman |
| 2011/0188629 | A1 | 8/2011 | Meng |
| 2012/0061581 | A1 | 3/2012 | Hugg et al. |
| 2013/0161520 | A1 | 6/2013 | Jansen |
| 2013/0251100 | A1* | 9/2013 | Sasaki .................. G01N 23/046 378/20 |
| 2016/0116604 | A1 | 4/2016 | Zeraatkar et al. |

FOREIGN PATENT DOCUMENTS

| | | |
|---|---|---|
| CN | 105806860 A | 7/2016 |
| CN | 107315019 A | 11/2017 |
| EP | 1933170 A1 | 6/2008 |
| JP | H10-162762 A | 6/1998 |
| JP | 2006-519647 A | 8/2006 |
| JP | 2007-232530 A | 9/2007 |
| JP | 2008-256587 A | 10/2008 |
| JP | 2010-025711 A | 2/2010 |
| JP | 2013-190333 A | 9/2013 |
| JP | 2015-200649 A | 11/2015 |
| WO | WO 2004/078043 A1 | 9/2004 |
| WO | WO 2015/029144 A1 | 3/2015 |

OTHER PUBLICATIONS

Japan Patent Application No. 2018-139648; Notice of Reasons for Refusal; dated May 8, 2019; 17 pages.

Golosio et al.; "Internal elemental microanalysis combining x-ray fluorescence, Compton and transmission tomography"; Journal of Applied Physics; vol. 94 No. 1; Jul. 2003; p. 145-156.

Great Britain Patent Application No. 1812115.2; Combined Search and Examination Report; dated Jan. 22, 2019; 7 pages.

* cited by examiner

RAY TRANSMISSION AND FLUORESCENCE CT IMAGING SYSTEM AND METHOD

CROSS-REFERENCE TO RELATED APPLICATION(S)

This application claims priority to the Chinese Patent Application No. 201710616773.6, filed on Jul. 25, 2017, which is incorporated herein by reference in its entirety.

TECHNICAL FIELD

The present disclosure relates to radiation imaging, and more particularly, to a ray transmission and florescence Computed Tomography (CT) imaging system and method.

BACKGROUND

The X-ray CT imaging technology has achieved great success in many fields such as clinical medicine, security inspection, industrial non-destructive detection etc. A basic principle of the X-ray CT imaging in the related art is to scan an object at different angles using a beam of X rays emitted by an X-ray source, measure information (energy integral, a number of photons, etc.) before and after the beam of X rays passes through the object, establish a physical model using a difference between the two pieces of information, and then obtain a distribution image of equivalent linear attenuation coefficients of substances in the scanned object through CT image reconstruction, i.e., a gray image representing intensity of absorption of substances relative to the X rays. However, this imaging method has no specificity and uniqueness, and thus cannot achieve accurate substance recognition. In the past ten years, the X-ray energy spectrum CT (including dual-energy CT) technology has made great progress, which can obtain, in addition to a distribution image of equivalent linear attenuation coefficients in an object under different energies, distribution images of equivalent atomic numbers and electron densities of the object by acquiring X-ray projection data under two or more different energies (energy spectrums) through CT reconstruction and material decomposition algorithms. Thus, the X-ray energy spectrum CT technology has a certain substance recognition capability, and has gained important applications in application fields such as clinical medicine, security inspection etc.

Unlike the X-ray CT in the related art, the X-ray fluorescence CT is to irradiate an object using a beam of X rays with a certain energy, to excite some high-Z elements in the object to generate fluorescent photons with a particular energy to be emitted, which are detected by a detector. As each element corresponds to a unique X-ray fluorescence energy spectrum, accurate recognition of different elements can be achieved by the acquired fluorescence energy spectrum data. The fluorescence CT is to acquire fluorescent photons generated by performing X-ray scanning on an object at different angles, and achieve high sensitivity recognition and quantitative calculation of specific elemental substances through image reconstruction. Up to now, researches on the fluorescence CT in the word are mainly divided into two categories. A first one of the two categories is fluorescence CT researches based on a synchrotron radiation source, which mainly use extremely high brightness and monochromaticity of the synchrotron radiation source. However, due to a large volume and a high cost of a synchrotron radiation system, it is not suitable for engineering application researches. A second one of the two categories is XFC researches based on an ordinary X-ray machine, wherein an energy spectrum of X rays generated by the X-ray machine has continuous characteristics, and due to its low price and small volume, the X-ray machine has become a mainstream of the current fluorescence CT researches. However, the current fluorescence CT imaging system based on an X-ray machine generally uses a single-pixel X-ray spectrometer with a high energy resolution to detect fluorescent photons in order to improve the efficiency of acquisition of the fluorescent photons and reduce noises. A single-hole collimator is provided in front of the X-ray machine or in front of the X-ray spectrometer to determine a path of the rays, and the first-generation CT scanning method with a very low efficiency, i.e., a "rotation+translation" type scanning method, is used to complete acquisition of fluorescence CT data. Therefore, a scanning time of several or even a dozen hours is required, which thus cannot meet the requirements of engineering applications.

SUMMARY

In order to solve the above problems, the present disclosure proposes a ray transmission and fluorescence CT imaging system and method, which realize transmission CT imaging and fluorescence CT imaging for an object simultaneously through one circumferential scanning based on the third generation CT scanning method.

In an aspect of the present disclosure, there is proposed a ray transmission and fluorescence Computed Tomography (CT) imaging system, comprising: a ray source configured to emit a beam of rays; a rotational scanning device configured to perform rotational CT scanning on an object to be inspected; a transmission CT detector configured to receive the beam of rays which has passed through the object to be inspected after being emitted by the ray source; a fluorescence CT detector configured to receive fluorescent photons excited by irradiation of the beam of rays emitted by the ray source on the object to be inspected; a data acquisition unit configured to acquire a transmission data signal from the transmission CT detector and a fluorescence data signal from the fluorescence CT detector respectively; and a control and data processing unit configured to control the ray source to emit the beam of rays, control the rotational scanning device to perform the rotational CT scanning on the object to be inspected, and obtain a transmission CT image and a fluorescence CT image simultaneously based on the transmission data signal and the fluorescence data signal.

In an embodiment, the control and data processing unit controls the rotational scanning device, the transmission CT detector, and the fluorescence CT detector to perform the rotational CT scanning on the object to be inspected.

In an embodiment, the fluorescence CT detector comprises: a fluorescence energy spectrum detection element; a collimator configured to collimate the excited fluorescent photons on the fluorescence energy spectrum detection element; and a shielding member configured to enclose the fluorescence energy spectrum detection element.

In an embodiment, the shielding member is formed of a high density material, and the collimator is formed on sidewalls of the shielding member.

In an embodiment, a distance between the collimator and the fluorescence energy spectrum detection element and a length of the fluorescence energy spectrum detection element are adjustable.

In an embodiment, the collimator is a collimation hole, and the excited fluorescent photons are collimated through the collimation hole onto the fluorescence energy spectrum detection element.

In an embodiment, the collimation hole has an opening inclination angle of 90 degrees and a central aperture of 0.5 mm in diameter.

In an embodiment, the fluorescence energy spectrum detection element is a line array detection element or an area array detection element.

In an embodiment, the ray source is an apparatus capable of emitting X rays or γ rays.

In an embodiment, the transmission CT detector is a line array detector or an area array detector.

In an embodiment, the control and data processing unit calculates a linear attenuation coefficient distribution related to the object to be inspected according to the transmission data signal and a transmission intensity model.

In an embodiment, the control and data processing unit calculates a concentration distribution or a component distribution of a specific element related to the object to be inspected according to the fluorescence data signal, a fluorescence intensity model, and the linear attenuation coefficient distribution.

In an embodiment the control and data processing unit performs image fusion processing on the obtained transmission CT image and fluorescence CT image.

In another aspect of the present disclosure, there is proposed a ray transmission and fluorescence Computed Tomography (CT) imaging method, comprising steps of: emitting, by a ray source, a beam of rays; performing, by a rotational scanning device, rotational CT scanning on an object to be inspected; acquiring, by a data acquisition unit, a transmission data signal from a transmission CT detector and a fluorescence data signal from a fluorescence CT detector respectively; and obtaining a transmission CT image and a fluorescence CT image simultaneously based on the transmission data signal and the fluorescence data signal.

In an embodiment, performing by a rotational scanning device rotational CT scanning on an object to be inspected comprises: performing, by the rotational scanning device, the transmission CT detector, and the fluorescence CT detector, the rotational CT scanning on the object to be inspected.

In an embodiment, obtaining a transmission CT image and a fluorescence CT image simultaneously based on the transmission data signal and the fluorescence data signal comprises calculating a linear attenuation coefficient distribution related to the object to be inspected based on the transmission data signal and a transmission intensity model.

In an embodiment, obtaining a transmission CT image and a fluorescence CT image simultaneously based on the transmission data signal and the fluorescence data signal comprises calculating a concentration distribution or a component distribution of a specific element related to the object to be inspected based on the fluorescence data signal, a fluorescence intensity model, and the linear attenuation coefficient distribution.

In an embodiment, the step of calculating a concentration distribution of a specific element related to the object to be inspected comprises: if the ray source uses single-energy CT scanning, an attenuation coefficient distribution $\mu(E, \vec{r})$ of fluorescence is replaced approximately by an attenuation coefficient distribution $\bar{\mu}(\vec{r})$ of the rays; and if the ray source uses multi-energy CT scanning, the attenuation coefficient distribution $\mu(E, \vec{r})$ of the fluorescence is approximately replaced by an attenuation coefficient distribution $\mu(E_k, \vec{r})$ of the rays in each energy region, where k represents a number of an energy region of a ray detector, $E_k$ represents an average energy of photons in a $k^{th}$ energy region, and $\vec{r}$ is a position in the object to be inspected.

In an embodiment, the method further comprises: performing image fusion processing on the obtained transmission CT image and fluorescence CT image.

With the above technical solution, the ray transmission CT imaging and the fluorescence CT imaging can be completed simultaneously in one complete scanning, thereby realizing fusion imaging using the two imaging methods. The imaging technology according to the present disclosure incorporates advantages of the X-ray CT in the related art such as a high speed, stability, a low cost etc., and advantages of Positron Emission Tomography (PET) and Single-Photon Emission Computed Tomography (SPECT) such as capability of reflecting human metabolism functional imaging, a high sensitivity etc., and can achieve rapid molecular functional imaging using non-radioactive drugs with biological specificity. The technology has great potential and application value in the fields such as biology, clinical medicine, security inspection etc.

BRIEF DESCRIPTION OF THE DRAWINGS

The following accompanying drawings illustrate implementations of the present disclosure. The accompanying drawings and the implementations provide some embodiments of the present disclosure in a non-limiting, non-exhaustive manner. In the accompanying drawings.

DETAILED DESCRIPTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

Figure 1:
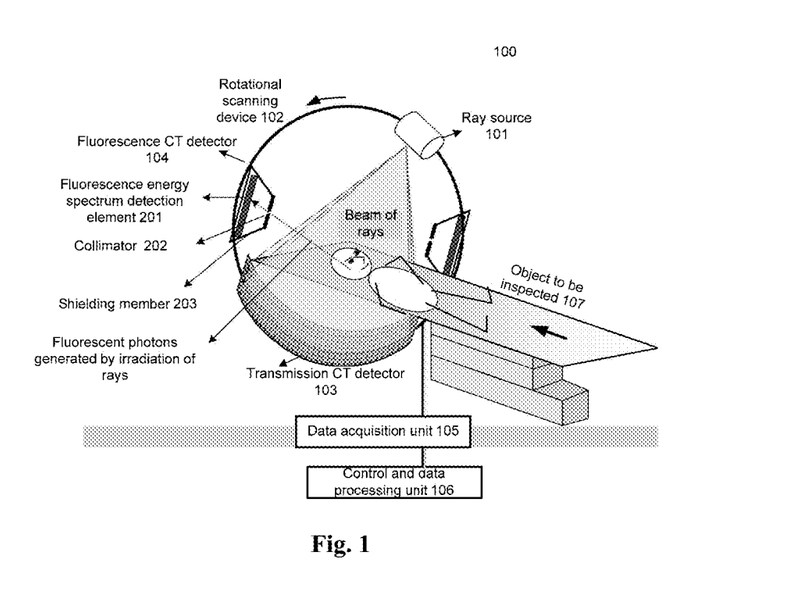
FIG. 1 is a structural diagram illustrating a ray transmission and fluorescence CT imaging system according to an embodiment of the present disclosure.

FIG. 1 is a structural diagram illustrating a ray transmission and fluorescence CT imaging system 100 according to an embodiment of the present disclosure. As shown in FIG. 1, the imaging system 100 according to the embodiment of the present disclosure comprises a ray source 101, a rotational scanning device 102, a transmission CT detector 103, a fluorescence CT detector 104, a data acquisition unit 105, and a control and data processing unit 106.

The ray source 101 emits a beam of rays. The ray source 101 may be various types of common X-ray machines, accelerators, or apparatuses capable of emitting X rays or γ rays, such as radioisotopes, synchrotron radiation sources etc.

The rotational scanning device 102 performs rotational CT scanning on an object 107 to be inspected. A core function of the rotational scanning device 102 is to complete a CT scanning process according to set scanning parameters. In clinical medicine CT and security inspection CT, rotational scanning is generally realized surrounding the object 107 to be inspected using core apparatuses such as a sliding ring structure, a rotational X-ray machine, a detector etc. In contrast, in industrial CT, CT scanning is generally realized by fixing the object to be inspected to a rotational platform to rotate the object.

The transmission CT detector 103 receives the beam of rays which has passed through the object 107 to be inspected after being emitted by the ray source 101. The transmission CT detector 103 may be an array detector for transmission CT, which may be an energy integral type detector in the related art, for example, a multi-row detector array based on a scintillator plus photomultiplier tube structure which currently is often used for medical spiral CT, or a flat panel detector, or an array energy spectrum detector, for example, an array of photon count detectors which currently is often used for researches.

The fluorescence CT detector 104 receives fluorescent photons excited by irradiation of the beam of rays emitted by the ray source 101 in the object 107 to be inspected. The fluorescence CT detector 104 may be realized by using an array energy spectrum detector for fluorescence CT. The array energy spectrum detector is used to distinguish fluorescent photons with a particular energy from scattered photons with other energies. The fluorescence CT detectors in the related art are mostly realized by using a single-pixel X-ray spectrometer with a high energy resolution but a very low scanning speed. In contrast, the array energy spectrum detector (for example, an array photon count detector) used in the embodiment of the present disclosure requires only a few energy windows to realize acquisition of the fluorescent photons with a particular energy. In the present embodiment, there may be a plurality of fluorescence CT detectors 104. For example, two fluorescence CT detectors as shown in FIG. 1 are located on the left side and the right side respectively, but the present embodiment is not limited thereto.

The data acquisition unit 105 acquires a transmission data signal from the transmission CT detector 103 and a fluorescence data signal from the fluorescence CT detector 104 respectively. In an embodiment, the data acquisition unit 105 acquires projection data generated by the transmission CT detector 103 and the fluorescence CT detector 104 during the CT scanning respectively.

The control and data processing unit 106 controls the ray source 101 to emit the beam of rays, controls the rotational scanning device 102 to perform the rotational CT scanning on the object 107 to be inspected, and obtains a transmission CT image and a fluorescence CT image simultaneously based on the transmission data signal and the fluorescence data signal. Specifically, the control and data processing unit 106 controls the rotational scanning device 102 to rotate the ray source 101, the transmission CT detector 103, and the fluorescence CT detector 104 to perform the rotational CT scanning on the object 107 to be inspected, and completes the simultaneous reconstruction of the transmission CT image and the fluorescence CT image of the present disclosure based on the acquired projection data generated by the transmission CT detector 103 and the fluorescence CT detector 104 during the CT scanning. Thereby, a fused image of the transmission CT image and the fluorescence CT image is displayed on a display.

Figure 2A:
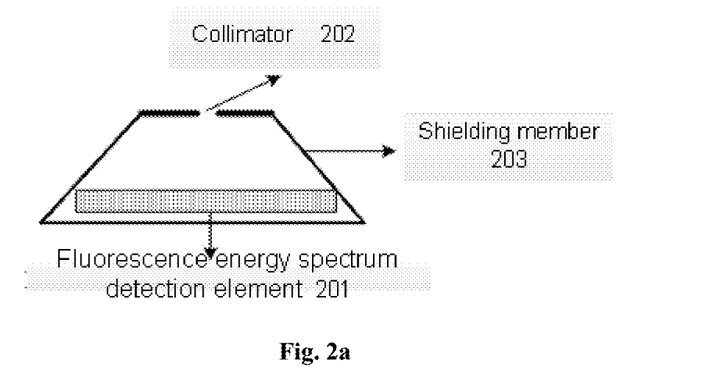
FIG. 2a is a structural diagram illustrating a fluorescence CT detector in the imaging system of FIG. 1 according to an embodiment of the present disclosure.

FIG. 2a is a structural diagram illustrating the fluorescence CT detector in the imaging system of FIG. 1 according to an embodiment of the present disclosure. The fluorescence CT detector 104 comprises a fluorescence energy spectrum detection element 201, a collimator 202, and a shielding member 203.

The fluorescence energy spectrum detection element 201 may distinguish the fluorescent photons with a particular energy from the scattered photons with other energies. The fluorescence CT in the related art mostly uses a single-pixel X-ray spectrometer with a high energy resolution but a very slow scanning speed. In contrast, the fluorescence energy spectrum detection element (for example, an array photon count detector) used in the embodiment of the present disclosure requires a few energy windows to realize acquisition of the fluorescent photons with a particular energy.

Figure 2B:
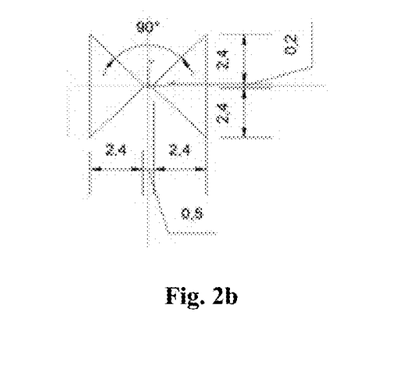
FIG. 2b is a detailed design diagram illustrating a collimator in the fluorescence CT detector of FIG. 2a according to an embodiment of the present disclosure.

The collimator 202 collimates the excited fluorescent photons of the X rays onto the fluorescence energy spectrum detection element 201. In the present embodiment, the collimator may be a collimation hole, through which, based on the principle of pinhole imaging, the fluorescent photons generated by irradiation of the rays on specific high-Z elements (Z indicates atomic number) are collimated onto the fluorescence energy spectrum detection element 201, so as to realize the acquisition of fluorescence on a corresponding straight path. The collimation hole and the fluorescence energy spectrum detection element are related to a size of a field of view of the fluorescence CT imaging, and different fields of view of the fluorescence CT imaging may be designed by adjusting a distance between the collimation hole and the fluorescence energy spectrum detection element and a length of the detection element. Therefore, the collimation hole is one of the devices capable of realizing large-field fluorescence CT imaging. FIG. 2b is a detailed design solution of the collimation hole, wherein an opening inclination angle is 70°-110°, and a central aperture may be 0.1 mm-5 mm in diameter. In an embodiment, the opening inclination angle is 90° and the central aperture is 0.5 mm in diameter.

The shielding member 203 encloses other portions of the fluorescence energy spectrum detection element 201 except for a portion where the collimator 202 is located. In an embodiment, the shielding member 203 is a shielding case which is formed of a high density material, and the collimator 202 is formed on sidewalls of the shielding member 203 as shown in FIG. 2a. In the present embodiment, the shielding member functions to seal the fluorescence energy spectrum detection element in a case of high-density material (for example, a lead-covered metal case), and set the collimation hole only on a small end surface of the shield case, so that photons incident in other directions through the collimation hole are blocked outside the shielding case while minimizing the influence of background scattered photons on the fluorescence energy spectrum detection element.

Figure 3:
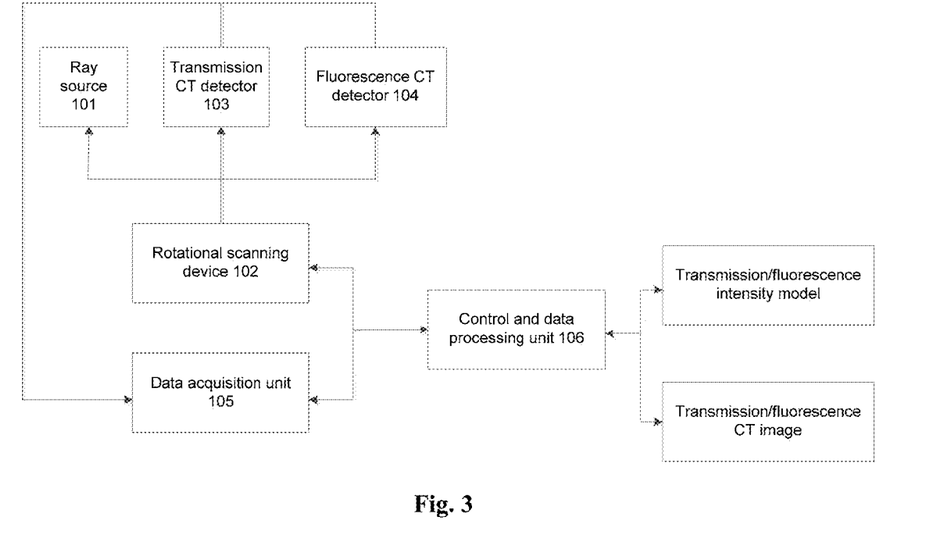
FIG. 3 is a logic diagram illustrating control and data processing of the imaging system shown in FIG. 1 according to an embodiment of the present disclosure.

FIG. 3 is a logic diagram illustrating control and data processing of the imaging system shown in FIG. 1 according to an embodiment of the present disclosure. The control and data processing unit 106 controls the ray source 101 to emit a beam of rays, and controls the rotational scanning device 102 to rotate the ray source 101, the transmission CT detector 103, and the fluorescence CT detector 104 to perform the rotational CT scanning on the object 107 to be inspected. The transmission CT detector 103 receives the beam of rays which has passed through the object 107 to be inspected after being emitted by the ray source 101, and the fluorescence CT detector 104 receives fluorescent photons excited by irradiation of the beam of rays emitted by the ray source 101 in the object 107 to be inspected. The data acquisition unit 105 acquires a transmission data signal from the transmission CT detector 103 and a fluorescence data signal from the fluorescence CT detector 104 respectively. The control and data processing unit 106 calculates a linear attenuation coefficient distribution related to the object to be inspected according to the transmission data signal and a transmission intensity model (a mathematical model for calculating X-ray transmission intensity). The control and data processing unit 106 further calculates a concentration distribution or a component distribution of a specific element (high-Z element) related to the object to be inspected according to the fluorescence data signal and a fluorescence intensity model (a mathematical model for calculating fluorescence intensity). In the present embodiment, the linear attenuation coefficient distribution is required for reconstruction of the concentration distribution or the component distribution, thereby completing the simultaneous reconstruction of the transmission CT image and the fluorescence CT image of the present disclosure, and displaying a fused image of the transmission CT image and the fluorescence CT image on a display. The fused image comprises not only linear attenuation coefficient distribution information (which may be represented in grayscale) but also an atomic number of a specific element and corresponding concentration distribution information (which may be represented in color and corresponding brightness).

Figure 4:
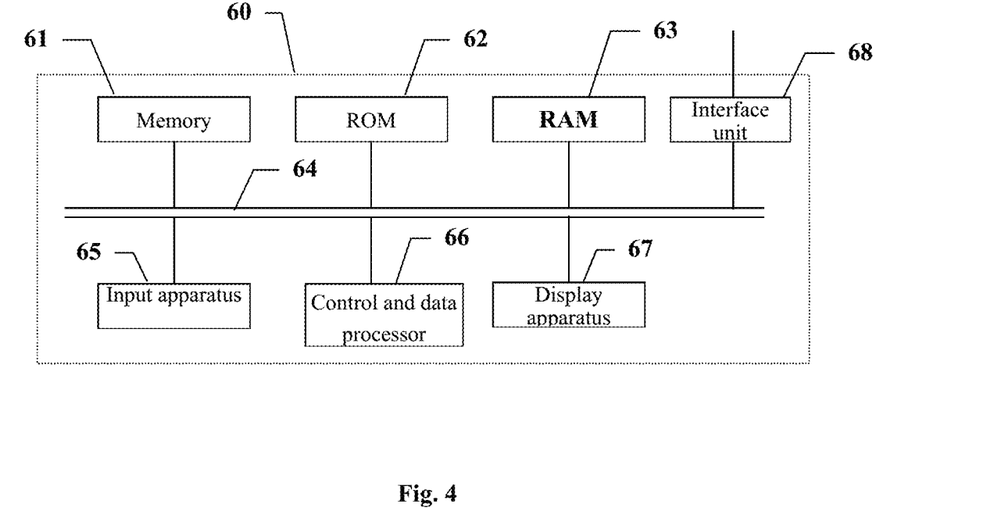
FIG. 4 is a structural block diagram illustrating a computer comprising a control and data processing unit of FIG. 1 according to an embodiment of the present disclosure.

FIG. 4 is a structural block diagram illustrating a computer comprising the control and data processing unit of FIG. 1 according to an embodiment of the present disclosure. As shown in FIG. 4, data acquired by the data acquisition unit is stored in a memory 61 via an interface unit 68 and a bus 64. An intensity model is also stored in the memory 61. Configuration information and programs of a computer data processor are stored in a Read Only Memory (ROM) 62. A Random Access Memory (RAM) 63 is used to temporarily store various data during an operation of a control and data processor 66. In addition, a computer program for performing data processing is also stored in the memory 61. The internal bus 64 is connected to the memory 61, the read only memory 62, the random access memory 63, an input apparatus 65, the processor 66, a display apparatus 67, and the interface unit 68. After a user inputs an operation command through the input apparatus 65 such as a keyboard, a mouse etc., instruction codes of the computer program instruct the processor 66 to execute a predetermined image reconstruction algorithm, and after obtaining a data processing result, display the data processing result on the display apparatus 67 such as an LCD display etc. or directly output the processing result in a form of a hard copy such as printing etc.

Figure 5:
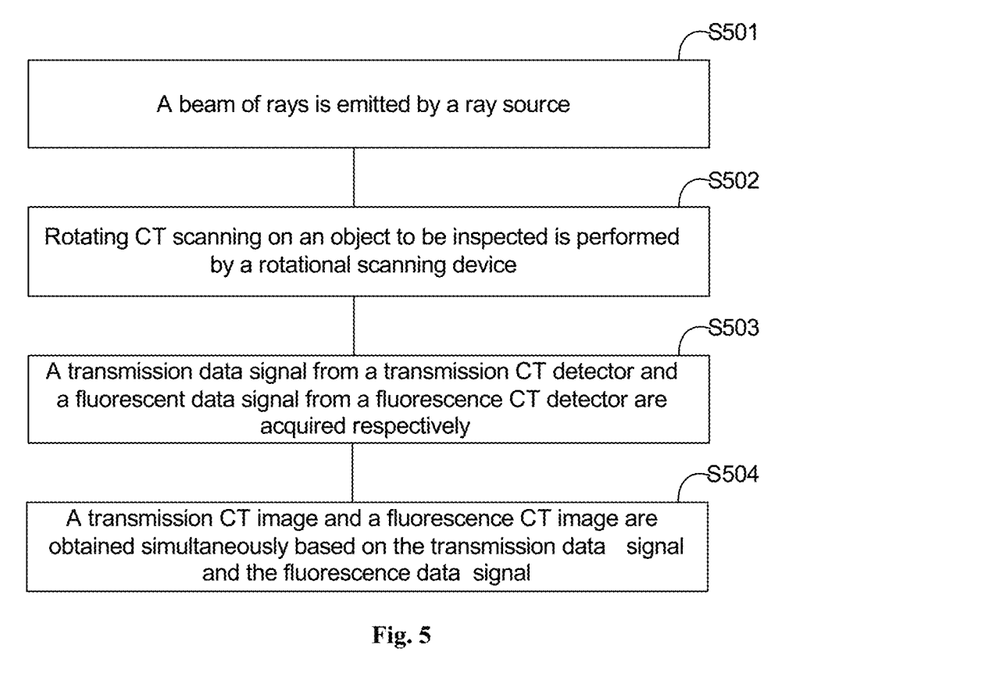
FIG. 5 is a flowchart illustrating a ray transmission and fluorescence CT imaging method according to an embodiment of the present disclosure.

FIG. 5 is a flowchart illustrating a CT imaging method for imaging both transmitted rays and excited fluorescence according to an embodiment of the present disclosure.

In step 501, a beam of rays is emitted by a ray source.

In step 502, rotating CT scanning on an object to be inspected is performed by a rotational scanning device.

In step 503, a transmission data signal from a transmission CT detector and a fluorescent data signal from a fluorescence CT detector are acquired respectively.

In step 504, a transmission CT image and a fluorescence CT image are obtained simultaneously based on the transmission data signal and the fluorescence data signal.

In an embodiment, step 502 comprises controlling the rotational scanning device to rotate the ray source, the transmission CT detector, and the fluorescence CT detector to perform the rotational CT scanning on the object to be inspected.

In an embodiment, step 504 comprises calculating a linear attenuation coefficient distribution related to the object to be inspected based on the transmission data signal and a transmission intensity model. Step 504 further comprises calculating a concentration distribution or a component distribution of a specific element related to the object to be inspected based on the fluorescence data signal, a fluorescence intensity model, and the linear attenuation coefficient distribution.

The transmission intensity model and the fluorescence intensity model as well as the imaging process will be described in detail below.

Firstly, considering that a beam of X rays emitted by an X-ray source arrives at a position $\vec{r}_T$ in an object to be inspected, after the X rays are attenuated by the object to be inspected, an energy spectrum of the incident X rays may be expressed as:

$$I(E, \vec{r}_T) = I_0(E) \cdot e^{-\int_{l_{\overline{ST}}} \mu(E, \vec{r}) d\vec{r}} \quad (1)$$

where $l_{\overline{ST}}$ represents a path along which the X rays emitted by the X-ray source pass through the position $\vec{r}_T$, $I_0(E)$ represents an energy spectrum of the X rays which are emitted by the X-ray source before being irradiated to the object to be inspected, and $\mu(E, \vec{r})$ represents an energy-related X-ray attenuation coefficient at any point in the object to be inspected.

The transmission CT imaging is to acquire a signal generated by incidence of the beam of X rays onto the transmission detector along its straight line propagation direction, which may be expressed as:

$$I(E_k) = \int_{bin(E_k)} I_0(E) \cdot Q(E) \cdot e^{-\int_{l_{ST}} \mu(E,\vec{r})d\vec{r}} dE \quad (2)$$

where Q(EE) represents an energy response function of the detector, k represents a number of an energy region of the X-ray energy spectrum detector (for example, a photon count detector), and $E_k$ represents an average energy of photons in a $k^{th}$ energy region. When the transmission CT detector is realized by using an energy integral type detector, an energy region $bin(E_k)$ for energy integral in the above equation (2) is a width $(0, E_{max})$ of an energy spectrum of the incident X rays.

For the fluorescence CT imaging, the X rays arriving at the position $\vec{r}_T$ which are represented by the equation (1) have a certain probability of generating fluorescent photons with a particular energy according to the following equation:

$$I_{XRF}(\vec{r}_T) = \int_{E_K}^{E_{max}} I(E, \vec{r}_T) \cdot \omega \cdot \rho(\vec{r}_T) \cdot \mu_{pe}^m(E) dE \quad (3)$$

where $\mu_{pe}^m(E)$ represents a photoelectric absorption quality coefficient of a specific element relative to the X rays at the position $\vec{r}_T$, $\omega$ represents a yield of the fluorescent photons (which may be approximated as a known constant), $\rho(\vec{r}_T)$ is a mass concentration of the specific element (for example, a contrast media) capable of generating fluorescence at the position, and $E_k$ represents a K-edge energy of the specific element.

The fluorescent photons generated above are acquired by the fluorescence CT energy spectrum detector shown in FIG. 2a, and a signal thereof may be expressed as:

$$I_{XFCT} = \int_{l_T} I_{XRF}(\vec{r}_T) \cdot \int_{Ang} e^{-\int_{l_{TD}} \mu_{XRF}(\vec{r})d\vec{r}} d\gamma d\vec{r}_T \quad (4)$$

where $l_{\overline{TD}}$ represents a path along which fluorescence generated at $\vec{r}_T$ is incident on a certain unit of the fluorescence energy spectrum detection element through the collimator, $\mu_{XRF}(\vec{r})$ represents a linear attenuation coefficient of the object to be inspected relative to the fluorescent photons, Ang represents a solid angle of $\vec{r}_T$ corresponding to the detector unit, and $l_T$ represents a straight path of the fluorescent photons acquired by the detector unit.

It can be seen from the above equation that the mathematical intensity model of the transmission CT is established by the equation (2), and the mathematical intensity model of the fluorescence CT is established by the equations 1, 3 and 4. A relationship between the two mathematical intensity models is that their signals are both from the same X-ray source $I_0(E)$ and are both related to the linear attenuation coefficient distribution $\mu(E, \vec{r})$ of the object to be inspected. An image reconstruction task according to the embodiment of the present disclosure comprises two parts which are a task of reconstructing $\mu(E, \vec{r})$ for the transmission CT imaging, and a task of reconstructing a concentration distribution $\rho(\vec{r}_T)$ of the specific element for the fluorescence CT imaging.

Firstly, considering reconstruction of a transmission CT image, it is also divided into two cases. A first one of the two cases is that if the transmission CT is single-energy spectrum CT scanning (which is currently a scanning method for most CTs), the equation (2) may be simplified as:

$$I = I_0 e^{-\int_{l(\vec{r})} \overline{\mu}(\vec{r})d\vec{r}} \quad (5)$$

At this time, an equivalent linear attenuation coefficient distribution $\overline{\mu}(\vec{r})$ of the object to be inspected may be reconstructed by a series of X-ray projection data acquired through complete CT scanning, i.e., $$\int_{l(\vec{r})} \overline{\mu}(\vec{r})d\vec{r} = -\ln\frac{I}{I_0} \quad (6)$$

where $I_0$ and I are intensities (energy integrals) of each X ray emitted by the X-ray source before and after passing through the object to be inspected.

A second one of the two cases is that if the transmission CT is multi-energy CT scanning (for example, dual-energy CT, energy spectrum CT, etc.), the equation (2) may be approximated as:

$$\int_{l(\vec{r})} \mu(E_k, \vec{r})d\vec{r} \approx -\ln\frac{I(E_k)}{I_0(E_k)} \quad (7)$$

Therefore, both the transmission CT equations (6) and (7) may be used to reconstruct a transmission CT image $\overline{\mu}(\vec{r})$ or $\mu(E_k, \vec{r})$ using a filtered back projection algorithm or an iterative reconstruction algorithm in the related art.

The reconstruction of the fluorescence CT is more complicated than that of the transmission CT. Firstly, a fluorescence intensity distribution $I_{XRF}(\vec{r})$ generated by irradiation on the object to be inspected is reconstructed using data IXFCT acquired by the fluorescence CT according to the equation (4). At this time, attenuation and absorption of the object itself relative to the fluorescence must be considered, that is, the influence of $\mu_{XRF}(\vec{r})$. Generally, $\mu_{XRF}(\vec{r})$ is provided by a reconstruction result of the transmission CT. If the transmission CT is single-energy CT scanning, $\mu_{XRF}(\vec{r})$ is approximated by $\overline{\mu}(\vec{r})$; and if the transmission CT is multi-energy CT scanning, $\mu_{XRF}(\vec{r})$ is approximated by an image $\mu(E_k, \vec{r})$ in an energy region where $E_k$ is closest to the energy of the fluorescent photons. Under the premise of known $\mu_{XRF}(\vec{r})$, the equation (4) may be approximated as:

$$I_{XFCT} = \int_{l_T} I_{XRF}(\vec{r}_T) \cdot \text{Map}_{AttXrf}(\vec{r}_T) d\vec{r}_T \quad (8)$$

where $\text{MaP}_{AUXrf}(\vec{r}_T)$ represents attenuation of the fluorescence generated at $\vec{r}_T$ before entering the detector. Considering that there is generally a small number of photons which may be acquired by the fluorescence CT, the fluorescence intensity distribution $I_{XRF}(\vec{r})$ of the object to be inspected may be reconstructed by the following equation in consideration of a Poisson noise model:

$$I_{XRF\_j}^{(k+1)} = \frac{I_{XRF\_j}^{(k)}}{\sum_{i=1}^{M} a_{ij}} \sum_{i=1}^{M} \frac{a_{ij} I_{XFCT\_i}}{\sum_{j'=1}^{N} a_{ij'} I_{XRF\_j'}^{(k)} \text{Map}_{AttXrf\_j'}} \quad (9)$$

where $a_{ij}$ represents a projection matrix determined by a spatial geometric relationship of the fluorescence CT imaging, i.e., contribution of an $i^{th}$ fluorescence projection $I_{XFCT\_i}$ acquired by the fluorescence CT detector to a $j^{th}$ pixel of the fluorescence intensity distribution $I_{XRF}$ to be reconstructed.

Once the fluorescence intensity distribution $I_{XRF}(\vec{r})$ of the object to be inspected is reconstructed, the concentration distribution $\rho(\vec{r}_T)$ of the specific element (the contrast media) in the object to be inspected may be calculated according to the following equation (10):

$$\rho(\vec{r}_T) = \frac{I_{XRF}(\vec{r}_T)}{\int_{E_K}^{E_{max}} I(E, \vec{r}_T) \cdot \omega \cdot \mu_{pe}^m(E) dE} \quad (10)$$

where a denominator on the right side of the equal sign is $\mu_{pe}^m(E)$, $\omega$ is a known quantity for a specific known element, and $I(E, \vec{r}_T)$ may be calculated according to the equation (1). Similarly to the above approximation of $\mu_{XRF}(\vec{r})$, $\mu(E, \vec{r})$ in the equation (1) is also provided by the transmission CT, i.e., if the transmission CT is single-energy CT scanning, $\mu(E, \vec{r})$ is approximated by $\bar{\mu}(\vec{r})$; and if the transmission CT is multi-energy CT scanning, $\mu(E, \vec{r})$ is approximated by an energy spectrum CT image $\mu(E_k, \vec{r})$ in each energy region.

The imaging system according to the present disclosure acquires attenuation information of the beam of rays which has passed through the object to be inspected after being emitted by the ray source and characteristic X photons excited by irradiation of the beam of rays on some high-Z elements in the object simultaneously through rotational scanning, and obtains a ray transmission CT image and a fluorescence CT image simultaneously through image reconstruction. As the transmission CT may provide structural information of the object with a high spatial resolution, and the fluorescence CT may achieve high sensitivity concentration distribution imaging for specific elements (some specific high-Z elements), the imaging apparatus according to the present disclosure can provide high-quality multi-modal information images in fields such as clinical medicine, security inspection etc.

The foregoing detailed description has set forth various embodiments of the X-ray imaging system and method via the use of block diagrams, flowcharts, and/or examples. In a case that such diagrams, flowcharts, and/or examples contain one or more functions and/or operations, it will be understood by those skilled in the art that each function and/or operation within such block diagrams, flowcharts or examples may be implemented, individually and/or collectively, by a wide range of hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. A ray transmission and fluorescence Computed Tomography (CT) imaging system, comprising:
   a ray source configured to emit a beam of rays;
   a rotational scanning device configured to perform rotational CT scanning on an object to be inspected;
   a transmission CT detector configured to receive the beam of rays which has passed through the object to be inspected after being emitted by the ray source;
   a fluorescence CT detector configured to receive fluorescent photons excited by irradiation of the beam of rays emitted by the ray source on the object to be inspected;
   a data acquisition unit configured to acquire a transmission data signal from the transmission CT detector and a fluorescence data signal from the fluorescence CT detector respectively; and
   a control and data processing unit configured to control the ray source to emit the beam of rays, control the rotational scanning device to perform the rotational CT scanning on the object to be inspected, and obtain a transmission CT image and a fluorescence CT image simultaneously based on the transmission data signal and the fluorescence data signal;

wherein the fluorescence CT detector comprises:

a fluorescence energy spectrum detection element;

a collimator configured to collimate the excited fluorescent photons of the rays on the fluorescence energy spectrum detection element; and a shielding member configured to enclose the fluorescence energy spectrum detection element.

2. The imaging system according to claim 1, wherein the control and data processing unit controls the rotational scanning device, the transmission CT detector, and the fluorescence CT detector to perform the rotational CT scanning on the object to be inspected.

3. The imaging system according to claim 1, wherein the shielding member is formed of a high density material, and the collimator is formed on sidewalls of the shielding member.

4. The imaging system according to claim 1, wherein a distance between the collimator and the fluorescence energy spectrum detection element and a length of the fluorescence energy spectrum detection element are adjustable.

5. The imaging system according to claim 1, wherein the collimator is a collimation hole, and the excited fluorescent photons are collimated through the collimation hole onto the fluorescence energy spectrum detection element.

6. The imaging system according to claim 5, wherein the collimation hole has an opening inclination angle of 90 degrees and a central aperture of 0.5 mm in diameter.

7. The imaging system according to claim 1, wherein the fluorescence energy spectrum detection element is a line array detection element or an area array detection element.

8. The imaging system according to claim 1, wherein the ray source is an apparatus capable of emitting X rays or γ rays.

9. The imaging system according to claim 1, wherein the transmission CT detector is a line array detector or an area array detector.

10. The imaging system according to claim 1, wherein the control and data processing unit calculates a linear attenuation coefficient distribution related to the object to be inspected according to the transmission data signal and a transmission intensity model.

11. The imaging system according to claim 10, wherein the control and data processing unit calculates a concentration distribution or a component distribution of a specific element related to the object to be inspected according to the fluorescence data signal, a fluorescence intensity model, and the linear attenuation coefficient distribution.

12. The imaging system according to claim 1, wherein the control and data processing unit performs image fusion processing on the obtained transmission CT image and fluorescence CT image.

13. A ray transmission and fluorescence Computed Tomography (CT) imaging method, comprising steps of:

emitting, by a ray source, a beam of rays;

performing, by a rotational scanning device, rotational CT scanning on an object to be inspected;

acquiring, by a data acquisition unit, a transmission data signal from a transmission CT detector and a fluorescence data signal from a fluorescence CT detector respectively; and obtaining a transmission CT image and a fluorescence CT image simultaneously based on the transmission data signal and the fluorescence data signal;

wherein the fluorescence CT detector comprises:

a fluorescence energy spectrum detection element;

a collimator configured to collimate the excited fluorescent photons of the rays on the fluorescence energy spectrum detection element; and a shielding member configured to enclose the fluorescence energy spectrum detection element.

14. The imaging method according to claim 13, wherein performing rotational CT scanning on an object to be inspected comprises: performing, by the rotational scanning device, the transmission CT detector, and the fluorescence CT detector, the rotational CT scanning on the object to be inspected.

15. The imaging method according to claim 13, wherein obtaining a transmission CT image and a fluorescence CT image simultaneously based on the transmission data signal and the fluorescence data signal comprises calculating a linear attenuation coefficient distribution related to the object to be inspected based on the transmission data signal and a transmission intensity model.

16. The imaging method according to claim 15, wherein obtaining a transmission CT image and a fluorescence CT image simultaneously based on the transmission data signal and the fluorescence data signal comprises calculating a concentration distribution or a component distribution of a specific element related to the object to be inspected based on the fluorescence data signal, a fluorescence intensity model, and the linear attenuation coefficient distribution.

17. The imaging method according to claim 16, wherein the step of calculating a concentration distribution of a specific element related to the object to be inspected comprises: if the ray source uses single-energy CT scanning, an attenuation coefficient distribution $\mu(E, \vec{r})$ of fluorescence is replaced approximately by an attenuation coefficient distribution, $\bar{\mu}(\vec{r})$ of the rays; and if the ray source uses multi-energy CT scanning, the attenuation coefficient distribution $\mu(E, \vec{r})$ of the fluorescence is approximately replaced by an attenuation coefficient distribution $\mu(E_k, \vec{r})$ of the rays in each energy region, where k represents a number of an energy region of a ray detector, $E_k$ represents an average energy of photons in a $k^{th}$ energy region, and $\vec{r}$ is a position in the object to be inspected.

18. The imaging method according to claim 13, further comprising:

performing image fusion processing on the obtained transmission CT image and fluorescence CT image.

* * * * *